United States Patent [19]

McDowell et al.

[11] Patent Number: 5,178,614
[45] Date of Patent: Jan. 12, 1993

[54] PROTECTIVE SHIELD FOR A STOMA POUGH

[76] Inventors: Charles E. McDowell, 1736 Still Water Glen, Escondido, Calif. 92026; Hugh E. Sorensen, 841 Westridge Way, Brea, Calif. 92621

[21] Appl. No.: 751,772

[22] Filed: Aug. 29, 1991

[51] Int. Cl.⁵ .............................................. A61F 5/44
[52] U.S. Cl. .................. 604/332; 604/340; 604/342
[58] Field of Search .................. 604/332–345

[56] References Cited

U.S. PATENT DOCUMENTS

| | | | |
|---|---|---|---|
| 1,922,763 | 8/1933 | Gricks | 604/340 |
| 2,549,649 | 7/1949 | Van Hove | 604/341 |
| 4,518,388 | 5/1985 | Jenson | 604/332 |
| 4,723,952 | 2/1988 | Esposito | 604/338 |
| 4,846,820 | 7/1989 | Jensen | 604/339 |
| 4,867,749 | 9/1989 | Steer | 604/337 |
| 4,872,215 | 10/1989 | Slinger | 2/2 |
| 4,929,245 | 5/1990 | Holtermann et al. | 604/338 |
| 5,004,464 | 4/1991 | Leise, Jr. | 604/330 |

FOREIGN PATENT DOCUMENTS 0100076  6/1962  Norway .............. 604/332

Primary Examiner—Randall L. Green
Assistant Examiner—R. Clarke

[57] ABSTRACT

An apparatus is provided for a protective shield for a stoma and a stoma collection pouch. The shield comprises a rigid thin shell portion having a convex exterior surface and a concave interior surface. A peripheral edge joins the two surfaces. A spring clip portion mounts onto a neck piece of the collection pouch and is attached to the peripheral edge of the shell portion such that the spring clip portion normally touches the concave surface of the shell portion and extends over the top of the collection pouch. The spring clip portion, when forced away from the shell portion, is urged to return toward the shell portion by spring action between the spring clip portion and the shell portion. The protective shield is positioned onto the collection pouch with the shell portion covering the outfacing external surface of that portion of the collection pouch surrounding the neck piece. The peripheral edge contacts the collection pouch surface and straddles the neck piece. The concave surface of the protective shield includes an adhesive layer which forms a bond with the outfacing external surface of the collection pouch such that the collection pouch is held in a fixed position with respect to the protective shield. The spring clip portion contacts the infacing external surface of the collection pouch adjacent the neck piece. The shell portion acts to prevent physical injury to the stoma and to the collection pouch.

9 Claims, 3 Drawing Sheets

PROTECTIVE SHIELD FOR A STOMA POUGH

FIELD OF THE INVENTION

This invention relates generally to protective covers and shields. More specifically, this invention relates to a protective shield for a stoma and a stoma waste collection pouch.

BACKGROUND OF THE INVENTION

Surgical procedures such as ileostomies, colostomies, and urostomies, frequently require that a portion of a patient's intestinal tract be diverted through an incision made in the skin of the abdominal area, thereby becoming a stoma. Typically, a collection pouch or similar appliance is adhered to the patient's skin immediately surrounding the stoma in order to collect waste materials which are discharged from the stoma at irregular and uncontrollable intervals. As such, it is important for such collection pouches to be continuously worn, for example, even while the patient is sleeping.

Various types of collection pouches and appliances are available to people with stomas. For example, one such device consists of a stoma face plate that is adhered to the skin immediately surrounding the stoma. A separate collection pouch is adapted to interlock with the face plate in order to provide a removable collection pouch with a leak-proof seal. One objective of this type of device is to provide an appliance that does not require a person to frequently affix and then remove an adhesive member to his skin. Another objective of such a device is to provide a locking mechanism between the face plate and the collection pouch that requires very little external pressure to achieve complete engagement or disengagement between the face plate and the collection pouch. As such, this device succeeds in raising the relative comfort level of a person with a stoma in that it is not necessary for the person to frequently apply strong pressure to the stoma or skin immediately surrounding the stoma.

However, one significant drawback to current stoma appliances is that, while care has been taken to reduced the amount of regular external force applied to the stoma area, very little has been done to prevent excessive force caused by unpredictable external events, such as one's rolling over while asleep, the inadvertent impact of a table corner while walking, or the wearing of an automotive restraint belt, and so forth. As a stoma has relatively few nerve endings, a stoma subjected to such excess external forces may not feel as though it has been damaged. Consequently, a person with a stoma whom inadvertently experiences excess force to the stoma area may not be aware than an injury has occurred. This frequently results in heavy bleeding for some time before the person becomes aware that he has an injury. Clearly, such situations can be embarrassing and potentially quite harmful.

There is a strong need, therefore, for a device that cooperates with existing stoma appliances and aids in protecting the sensitive and tender area of the stoma from excessive external force. Such a needed device would allow the normal operation of the collection pouch and would not be visually obtrusive, thereby resulting in a more secure feeling for the user of such a device. The present invention fulfills these needs and provides further related advantages.

SUMMARY OF THE INVENTION

The present invention is a protective shield for a stoma collection pouch that is attached to a stoma face plate flange. The pouch has a neck piece attached thereto for conducting a fluid, such as waste materials, into the pouch and for ready attachment to the stoma face plate flange. The shield comprises a rigid thin shell portion having a convex exterior surface and a concave interior surface. A peripheral edge joins the two surfaces.

A spring clip portion, preferably a pair of arms which partially encircle the neck piece, mounts onto the neck piece of the collection pouch and is attached to the peripheral edge of the shell portion such that the spring clip portion normally touches the concave surface of the shell portion and, preferably, extends over the top of the collection pouch. The spring clip portion, when forced away from the shell portion, is urged to return toward the shell portion by spring action between the spring clip portion and the shell portion. The protective shield is positioned onto the collection pouch with the shell portion covering the outfacing external surface of that portion of the collection pouch surrounding the neck piece. The peripheral edge contacts the collection pouch surface and straddles the neck piece. Preferably, the concave surface of the protective shield includes an adhesive layer which forms a bond with the outfacing external surface of the collection pouch such that the collection pouch is held in a fixed position with respect to the protective shield. The spring clip portion contacts the infacing external surface of the collection pouch adjacent the neck piece.

In operation, as the collection pouch swells during filling the spring clip portion flexes to allow a widening space between the shell portion and the spring clip portion. The shell portion acts to prevent physical injury to the stoma and the collection pouch.

This invention succeeds in protecting the stoma area and collection pouch area from inadvertent external impact. Moreover, this invention allows normal operation of the collection pouch while maintaining an unobtrusive external appearance under shirts, blouses, and other garments, resulting in a more secure feeling in the user. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
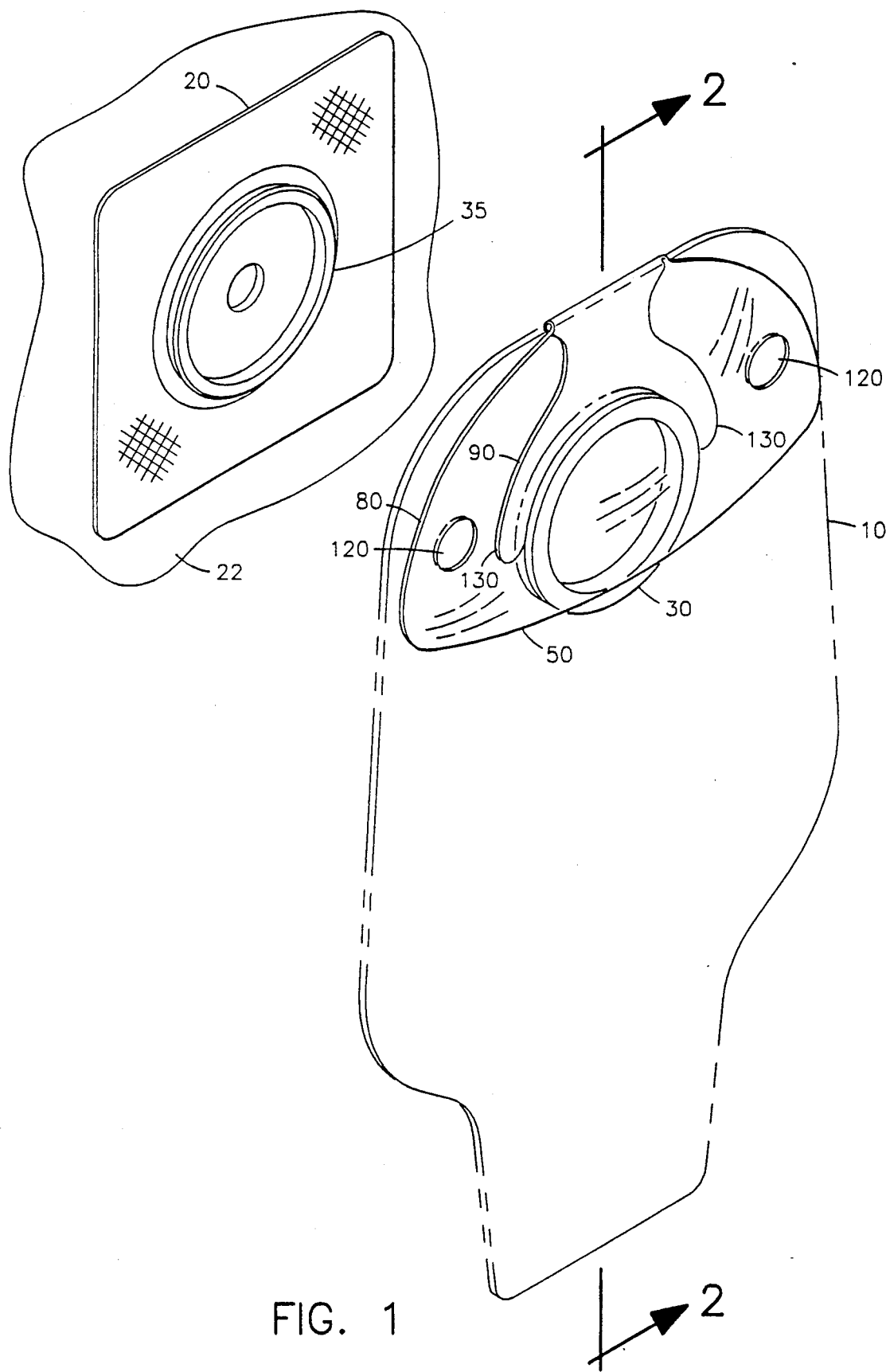
FIG. 1 is a perspective, partially exploded illustration of a shield of the present invention as mounted to a neck piece of a collection pouch, and a stoma face plate.
Figure 2:
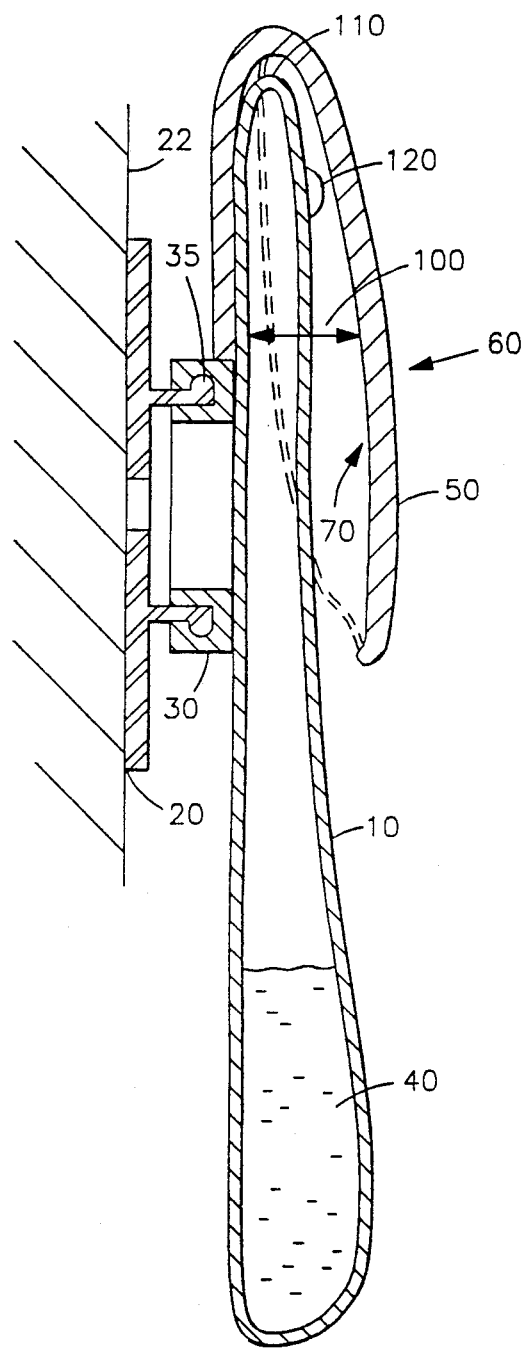
FIG. 2 is a cross-sectional view of a stoma collection appliance as used with the present invention, illustrating a protective shield thereof.

FIG. 1 shows a protective device for a stoma collection pouch 10, the collection pouch 10 being attached to a stoma face plate flange 35. The pouch 10 has a neck piece 30 attached thereto for conducting a fluid 40, such as waste materials, into the pouch 10 and for ready attachment to the stoma face plate flange 35. The shield comprises a rigid thin shell 50 having a convex exterior surface 60 and a concave interior surface 70 (FIG. 2). A peripheral edge 80 joins the two surfaces 60, 70.

A spring clip 90, preferably a pair of arms 130 which partially encircle the neck piece 30, mounts onto the neck piece 30 of the collection pouch 10 and is attached to the peripheral edge 80 of the shell 50 such that the spring clip 90 normally touches the concave surface 70 of the shell 50 and, preferably, extends over the top 110 of the collection pouch 10 (FIG. 2). The spring clip portion 90 and the shell portion 50 form a U-shaped assembly. The spring clip 90, when forced away from the shell 50, is urged to return toward the shell 50 by spring action between the spring clip 90 and the shell 50. The protective shield is positioned onto the collection pouch 10 with the shell 50 covering the outfacing external surface of that portion of the collection pouch 10 surrounding the neck piece 20. The peripheral edge 80 contacts the surface of the collection pouch 10 and straddles the neck piece 20. Preferably, the concave surface 70 of the protective shield includes an adhesive layer 120 which forms a bond with the outfacing external surface of the collection pouch 10 such that the collection pouch 10 is held in a fixed position with respect to the protective shield (FIG. 2). The spring clip 90 contacts the infacing external surface of the collection pouch 10 adjacent the neck piece 20.

Figure 3:
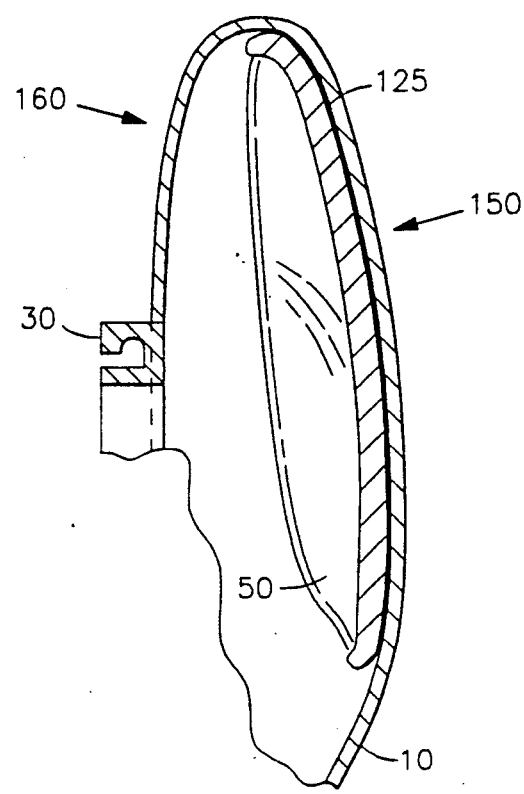
FIG. 3 is a cross-sectional view of a stoma collection appliance as used with an alternate embodiment of the present invention, illustrating a protective shield included within a collection pouch.
Figure 4:
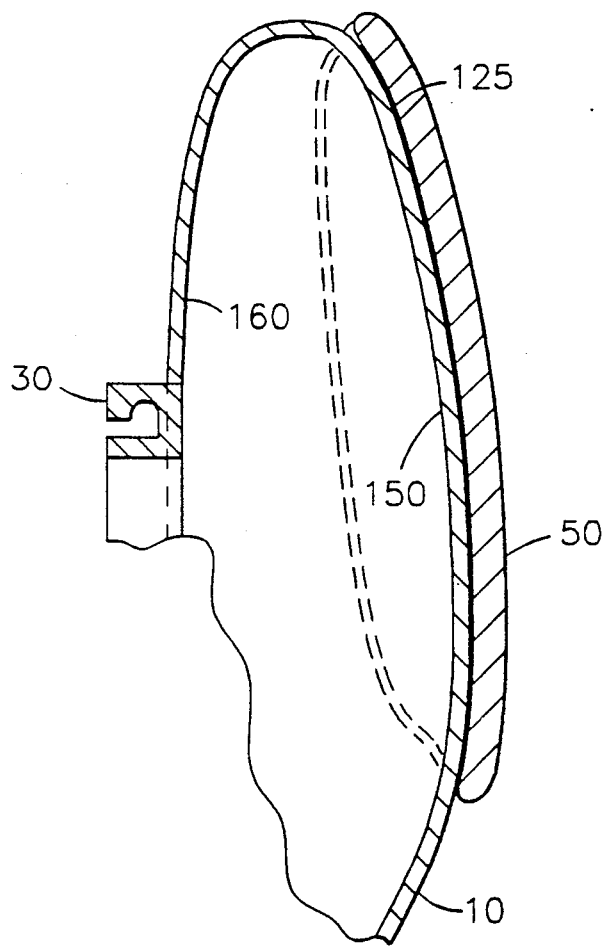
FIG. 4 is a cross-sectional view of a stoma collection appliance as used with an alternate embodiment of the present invention, illustrating a protective shield attached to the exterior surface of a collection pouch.

Preferably, the spring clip 90 and the shell portion 50 are manufactured from a rigid sheet material, such as plastic. In one embodiment of the invention, the plastic material is transparent, thereby facilitating visual guidance during the insertion of the shield over the collection pouch 10 and the placement of the spring clip 90 around the neck piece 30. In another embodiment of the invention, the shield of the present invention is fixedly attached to the neck piece 30 of the collection pouch 10, preventing the removal of the shield from the pouch neck piece 30. In an alternate embodiment of the invention whereby the pouch 10 is improved as a stoma protective devise, the shield is included inside the pouch 10, the pouch 10 having a front portion 150 and a rear portion 160 (FIG. 3), the shell 50 being attached to the pouch 10 by adhesive layer 125. An alternate configuration, FIG. 4, provides for the attachment of shell 50, alone, onto the exterior of pouch 10 by adhesive layer 125.

In operation, as the collection pouch 10 swells during filling the spring clip portion 90 flexes to allow a widening of space 100 between the shell portion 50 and the spring clip portion 90 (FIG. 2). The shell portion 50 acts to prevent physical injury to the stoma and to the collection pouch 10. Moreover, the protective shield of the present invention does not interfere with the tolerance fit between the neck piece 30 and the face plate flange 35.

While the invention has been described with reference to a few preferred embodiments, it is to be clearly understood by those skilled in the art that the invention is not limited thereto. Rather, the scope of the invention is to be interpreted only in conjunction with the appended claims.

I claim:

1. A combination protective device and a stoma collection pouch, the protective device comprising:
   a rigidly resilient thin shell having a convex exterior surface, a concave interior surface and a peripheral edge joining the two surfaces; and
   a means for attaching the shell to the collection pouch, the attachment means including a resilient spring clip for mounting the protective device onto a neck piece of the collection pouch, the spring clip extending integrally from the shell to form a U-shaped assembly, the clip being elastically urged to lay in contact with the concave surface for providing a clamping force for improved holding power of the protective device onto the neck piece, the neck piece being engaged between the clip and the concave surface, the convex exterior surface being positioned to provide a deflection means for preventing a puncture of the pouch and damage to the stoma.

2. The protective device for a stoma collection pouch of claim 1 further including an adhesive layer attached to the concave surface for adhering the shell to the pouch so that the shell is fixed in place on the pouch.

3. The protective device for a stoma collection pouch of claim 1 wherein the spring clip includes a pair of arms, the arms at least partially encircling the neck piece to secure the clip thereto.

4. The protective device for a stoma collection pouch of claim 1 wherein the clip is made of a transparent material to facilitate visibility when mounting the clip onto the neck piece.

5. A combination protective device and stoma collection pouch comprising:
   a stoma pouch including an enclosure for storing an effluent and a mounting neck piece for attaching the pouch to a stoma face plate flange;
   a rigidly resilient thin shell having a convex exterior surface, a concave interior surface and a peripheral edge joining
   a means for attaching the shell to the collection pouch, the attachment means including a resilient spring clip for mounting the protective device onto a neck piece of the collection pouch, the spring clip extending integrally from the shell to form a U-shaped assembly, the clip being elastically urged to lay in contact with the concave surface for providing a clamping force for improved holding power of the protective device onto the neck piece, the neck piece being engaged between the clip and the concave surface, the convex exterior surface being positioned to provide a deflection means for preventing a puncture of the pouch and damage to the stoma.

6. The combination stoma collection pouch and pouch protective device of claim 5 further including an adhesive layer attached to the concave surface for adhering the shell to the pouch so that the shell is fixed in place on the pouch.

7. The combination stoma collection pouch and pouch protective device of claim 5 wherein the spring clip includes a pair of arms, the arms at least partially encircling the neck piece to secure the clip thereto.

8. The combination stoma collection pouch and pouch protective device of claim 5 wherein the clip is made of a transparent material to facilitate visibility when mounting the clip onto the neck piece.

9. The combination stoma collection pouch and pouch protective device of claim 5 wherein the attachment means is an adhesive layer attached to the concave surface for adhering the shell to the pouch so that the shell is fixed in place on the pouch.

* * * * *